United States Patent [19]

Opitz et al.

[11] Patent Number: 4,643,877
[45] Date of Patent: Feb. 17, 1987

[54] FLUOROMETER

[75] Inventors: Norbert Opitz, Schwerte; Dietrich W. Lübbers, Dortmund, both of Fed. Rep. of Germany

[73] Assignee: Max Planck Gesellschaft zur Foerderung der Wissenschaften, Goettingen, Fed. Rep. of Germany

[21] Appl. No.: 638,883

[22] Filed: Aug. 8, 1984

[30] Foreign Application Priority Data

Aug. 12, 1983 [DE] Fed. Rep. of Germany ....... 3329257

[51] Int. Cl.$^4$ ............................................ G01N 21/64
[52] U.S. Cl. ........................................ 422/68; 422/52; 422/83; 356/246; 356/417; 356/437
[58] Field of Search ............... 422/68, 83, 52, 91; 436/169, 172; 250/364, 365, 458.1, 461.1, 461.2; 356/246, 419, 437

[56] References Cited

U.S. PATENT DOCUMENTS

| 2,551,542 | 5/1951 | Marsh et al. | 250/365 |
| 2,827,825 | 3/1958 | White | 356/246 |
| 3,200,254 | 8/1965 | VanLuik, Jr. et al. | 250/365 |
| 3,612,697 | 10/1971 | Nebe | 356/246 |
| 3,612,866 | 10/1971 | Stevens | 422/71 |
| 3,679,315 | 7/1972 | Laucournet et al. | 356/246 |
| 3,725,658 | 4/1973 | Stanley et al. | 422/83 |
| 3,795,489 | 3/1974 | Warnick et al. | 436/172 |
| 3,861,809 | 1/1975 | Hall, Jr. | 356/437 |
| 3,970,430 | 7/1976 | Reader, Jr. et al. | 356/437 |
| 4,066,362 | 1/1978 | Carter | 422/68 |
| 4,193,963 | 3/1980 | Bruening et al. | 436/172 |
| 4,218,141 | 8/1980 | Mayer | 356/246 |
| 4,220,415 | 9/1980 | Staab et al. | 356/246 |

FOREIGN PATENT DOCUMENTS 46885  4/1977  Japan ................................. 356/417

Primary Examiner—David L. Lacey
Attorney, Agent, or Firm—Michael J. Striker

[57] ABSTRACT

In order to increase measuring sensitivity of a fluorometer, a transmitter of monochromatic test light beam is arranged opposite a receiver of a measuring light beam. A measuring chamber including a fluorescent indicator space is arranged between the transmitter and the receiver. The distance between the transmitter and the receiver is adjustable to match to the thickness of the measuring chamber.

12 Claims, 5 Drawing Figures

FLUOROMETER

BACKGROUND OF THE INVENTION

The present invention relates in general to a fluorometer and in particular to a fluorometer of the type including a transmitter of a monochromatic light beam, a receiver of a monochromatic light beam, and a measuring chamber enclosing a space containing fluorescent indicators and including means for introducing an object of measurement into an effective contact with the indicator space.

The measuring principle of the fluorometer of this kind is based on quenching fluorescent radiation due to the effect of physical or chemical parameters of articles under measurement on the fluorescent radiation of the indicator. In this manner, changes in concentration or of parameters of the object of measurement can be determined. It is the quenching constant K defining the measuring sensitivity of the indicators for the concentration or parameter changes of the measured substance which is characteristic for the measuring process of this kind.

Fluorometers having the above-described features are extensively used in those fields where diverse measuring tasks are to be accomplished with the same measuring device. For different measuring requirements, it is sufficient to exchange the measuring chamber or the indicator space in the chamber only while the optical and light measuring devices remain the same.

Nevertheless, there are measuring tasks such as for example consecutive measurements in medical and biological fields in which highly specialized measuring devices are needed having a technological quality which is best suited to these measuring problems.

Especially in measuring transparent media, both solid or liquid or gaseous which exhibit only a minute fluorescent radiation, a transluminescent measuring device is employed with advantage. Fluoroscopy or measurement by transillumination is known from U.S. Pat. Nos. 3,725,658, and 3,612,866.

SUMMARY OF THE INVENTION

A general object of this invention is to improve the measurement using fluoroscopy.

In particular, it is an object of the invention to provide an improved fluorometer in which a maximum solid angle of the fluorescent radiation is effectively utilized.

Another object of this invention is to improve signal to noise ratio of the output signal.

In keeping with these objects and others which will become apparent hereafter, one feature of the invention resides, in the provision of a fluorometer which comprises a transmitter of a monochromatic light beam, a receiver of a monochromatic light beam, a measuring chamber including two opposite windows delimiting an indication space therebetween, the indicator space containing fluorescent indicators, and means for introducing an object of measurement in effective contact with the indicator space, and the transmitter and receiver of a monochromatic light beam being arranged adjacent respective windows so that the distance between the transmitter and the receiver correspond substantially to the thickness of the measuring chamber.

By virtue of this arrangement, the receiver is exposed to radiation from the indicator space at a maximum solid angle which is limited only by the thickness of the layer of the object of measurement in the measuring chamber.

The resulting substantial improvement of the signal to noise ratio of the output signal permits the use of indicators which hitherto due to their inferior measuring sensitivity could not be employed in many applications. Since the invention makes it possible to select a substantially increased number of indicators, it is now possible to measure types of particles or physical or chemical parameters which cannot be employed in prior art fluorometers.

For example, the novel measuring arrangement is operable with fluorescent indicators having quenching constant (K value) of $10^{-3}$/Torr to $10^{-5}$/Torr, whereas prior art measuring arrangements have been limited to indicators having K value between $10^{-1}$/Torr to $10^{-3}$/Torr in order to generate detectable signals.

Moreover, it is possible to use conventional sensitive fluorescence indicators in combination with transmitters emitting a light beam at a longer wavelength to which the indicators are less sensitive. This combination opens the possibility to make use of long wave transmitters, for example, light emitting diodes and also semiconductive light receiver. Due to the relatively limited intensity or photosensitivity of light emitting diodes, photodiodes or phototransmittors, the latter devices hitherto did not find application for operation in long wave ranges.

The monochromatization can be accomplished without problems by means of a filter. It is true that a filter diminishes the light signal intensity, nevertheless this drawback is freely compensated by the substantially increased sensitivity due to the arrangement of this invention. In the case when it is possible to employ the same wave length ranges both at the transmitter and at the receiver, the filters can be dispensed with.

While employing semiconductive elements for the light transmitters and receivers, it is now possible to design measuring devices which are substantially reduced in size, have a compact construction and a small consumption of energy. Consequently, portable measuring devices can be easily designed.

Since this invention enables the use of less sensitive fluoresent indicators, long time stability of the measuring arrangement is substantially higher than in prior art devices using sensitive indicators. Similarly, the linearity of less sensitive indicators is superior than that of the sensitive indicators. The latter features of the device of this invention represent substantial advantages in measuring technology.

Still another advantage is the increase of the measuring range during pH measurements. In conventional arrangements of this kind only narrow pH ranges, namely around the pH value of about 1.5 pH units are measurable because the intensity outside this narrow range considerably decreases. Since this invention enables the use of high radiation intensities, this limitation is no longer an obstacle and it is possible to measure also in pH ranges which extend far beyond the above pH values. Moreover, in comparison with prior art devices, this invention enables the measurement of thinner layers of the measured substance, thus achieving an improvement in the response time.

In further elaboration of this invention, the distance between the light transmitter and the measured light receiver is adjustable. In this manner, a minimum distance between the transmitter and the receiver is maintained even when using exchangeable measuring chambers of different thickness.

In addition, the thickness of the measuring chamber itself is adjustable. This modification results in a further optimization of the signal intensity.

With advantage, the indicator space adjoins the window of the measuring chamber which faces the light receiver so that the solid angle of received radiation is maximal. The concomittant decrease of the solid angle at the side of the transmitter is compensated by increased intensity of transmitted radiation.

Still another improvement of the measuring arrangement of this invention is achieved by designing the indicator space as a locally variable K value (quenching constant value) and shiftably arranging this indicator space within the measuring chamber.

By shifting such a variator of the quenching constant K relative to the path of the transmitted light beam, the quenching constant K is adjustable and can be optimized for a particular measurement.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERED EMBODIMENTS

Figure 1:
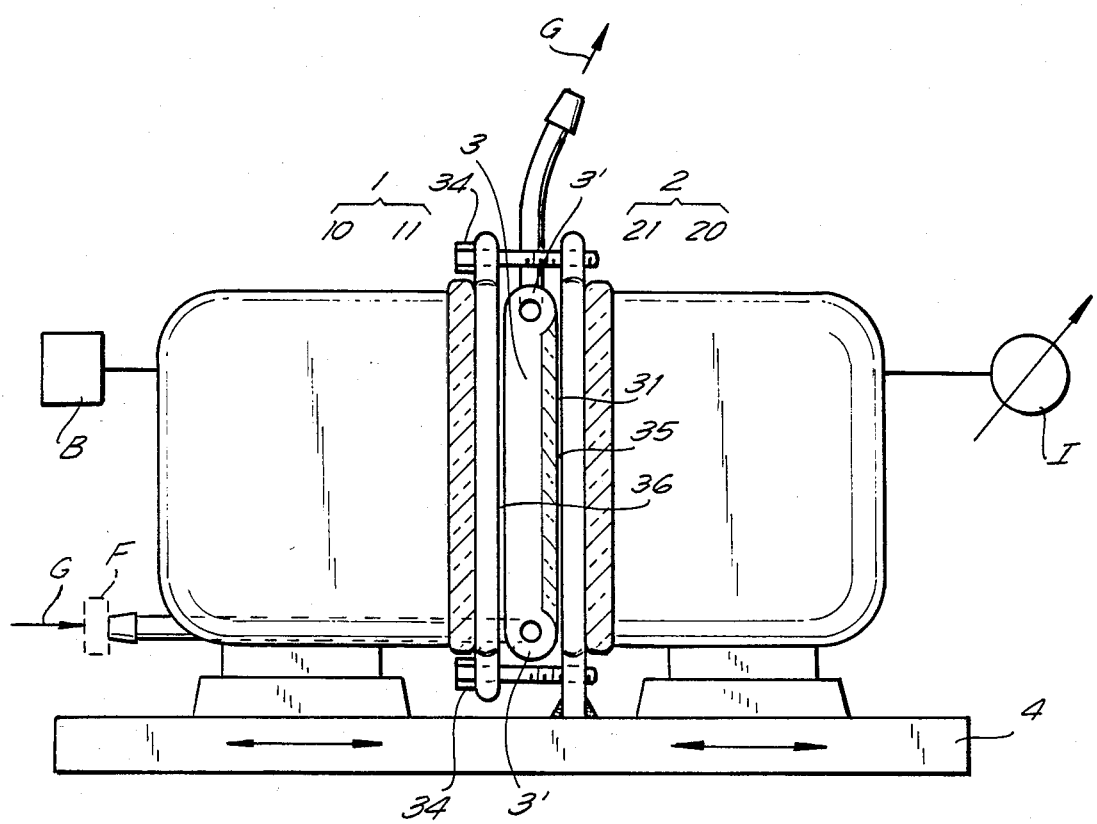
FIG. 1 is a measuring arrangement according to this invention.

In the arrangement of the fluorometer illustrated in FIG. 1, a light beam transmitter in the form a light emitting diode 10 is provided on its output side 11 with a monochromatic filter 11 to emit a beam of monochromatic light toward a juxtaposed photoelectric receiver 20. The output signal A from the receiver is indicated on an electric indicator. Source of electric power B power supplies the entire measuring arrangement. The input side of the photoelectric receiver 20 is also provided with a monochromatic filter 21, forming together a monochromatic receiver 2. The monochromatic light beam transmitter constituted by the light emitting diode and the monochromatic filter 11 is indicated by reference numeral 1. A measuring chamber 3, either in the form of a vessel or of a throughflow chamber, is arranged between the transmitter 1 and the receiver 2.

The illustrated measuring chamber 3 is designed with a relatively large cross-section so that a gas stream G which in this example represents and object of measurement, can be directed therethrough without obstructions. This kind of measuring chamber is suitable, for example for use in a breath analyzer which due to a small constant of the compact fluorometer of this invention can be readily realized.

With suitable modifications, the fluorometer can be also used for measuring transparent liquids.

To monitor the throughflow of the fluid in the measuring chamber, a flowmeter E can be used and a thermostat for stabilizing the temperature is also of advantage.

Preferably, the monochromatic transmitter 1 and/or the monochromatic receiver 2 are adjustably arranged on a base plate 4 so that both units can be adjusted as close to the measuring chamber 3 as possible. In a modification, the measuring chamber 3 and one of the units 1 or 2 are adjustably supported on the base plate.

Figure 3:
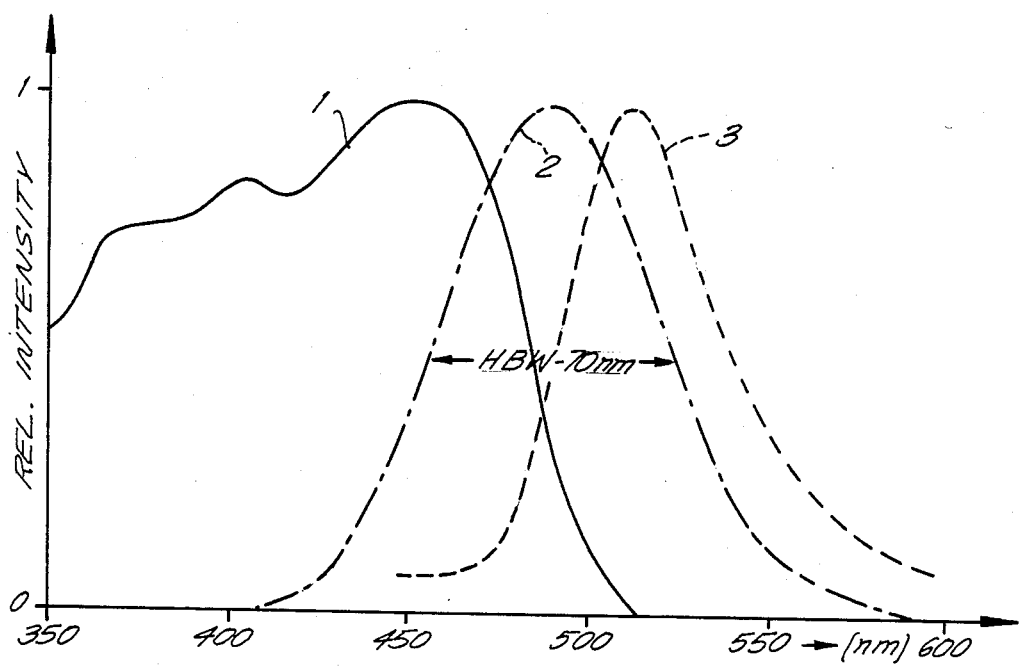
FIG. 3 is a plot diagram showing radiation intensity of a light emitting diode versus wavelength.

As mentioned before, both the light emitting diode 10 and the photoelectric receiver 20 are preferably in the form of semiconductive devices which both electrically and mechanically have superior mechanical and electrical quality. The disadvantage of semiconductive devices, namely the fact that they are most effective in the long wave range of the light spectrum, whereas most of the fluorescent indicators in the measuring chamber 3 operate in the short wave portion of the spectrum, as illustrated in FIG. 3, is compensated by high intensity of light radiation of the arrangement of this invention.

In the measuring chamber 3 there is provided an indicator space 31 frequently called an optode, which is in effective contact with the gaseous stream G. The optical properties of fluorescent indicators arranged in the indicator space 31 may vary in a known manner due to the interaction with the gaseous stream G, and these changes in the excited fluorescent light are detected by the monochromatic light receiver 2.

The intensity of the fluorescent radiation from the indicator space 31 can be increased by making the side walls 3' of the measuring chamber elastic and adjusting the thickness of the measuring chamber 3 by means of an adjustment mechanism 34 until a maximum output signal at the indicator I is obtained. In this manner, the measuring chamber is adjusted to its optimum thickness.

Windows 35 and 36 of the measuring chamber 3 facing respectively the transmitter 1 and the receiver 2, can be made in the form of optical monochromatic filters replacing the filters 11 and 21. The fluorescent indicators arranged in the indicator space 31 preferably have such a concentration that the excitation light beam from the transmitter is fully absorbed in the indicator space. In both cases the space between the photoelectric transmitter 10 and photoelectric receiver 20 (which need not be monochromatic) is reduced and consequently the intensity of measured light is increased. The mechanical adjustment device 34 which in this example is in the form of adjusting screws, threadingly engaging a holder of the measuring chamber are illustrated on an enlarged scale by way of an example only and in practice the holder is as thin as possible or constructed such as not to interfere with the adjustment of the distance between the transmitting and receiving units.

Figures 4, 4A:
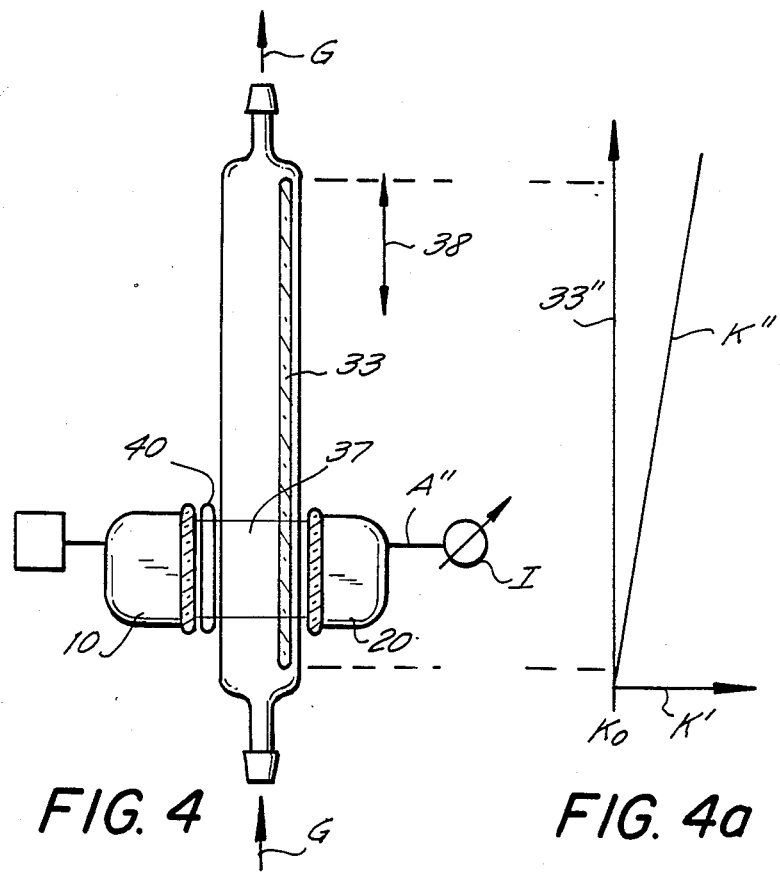
FIG. 4 illustrates an arrangement of this invention employing a variator of quenching constant K.
FIG. 4a is a plot diagram illustrating the relationship of K values to different lengths of the indicator space.

Provided that the thickness of the measuring chamber must not fall below a certain value, as is the case in a breath analyzer, then it is of advantage to focus the transmitted light beam by optical means 40 as illustrated in FIG. 4. The optical means are, for example, fresnel plates or lenses.

As can be seen from FIG. 3, the wavelength of radiation emitted by a cold light transmitter 1, such as, for example, light emitting diode 10, overlaps with the wavelength of applicable fluorescent indicators in measuring chamber 3 over a very narrow band only. In particular the excitation radiation for the indicators (curve 1), the fluorescent radiation of the indicators (curve 3), and the light emission of the light emitting diode (curve 2) overlap at a relatively low intensity in the wavelength range of about 470 nm. The low intensities in this case are compensated for by the high signal gain of the arrangement of this invention.

If desired, it is possible to use also different radiation sources when the resulting heat is withdrawn by suitable conventional means.

Figure 2:
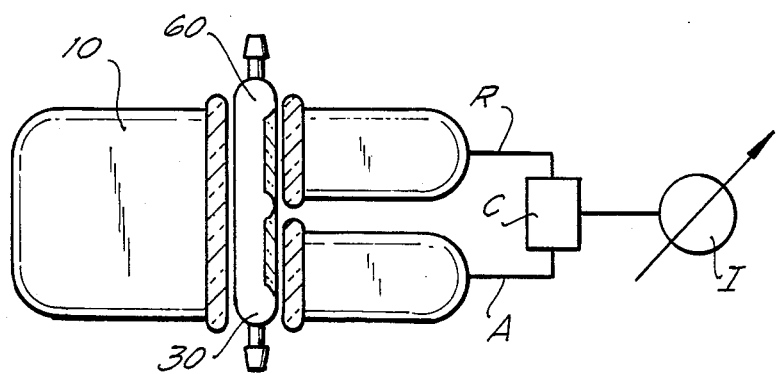
FIG. 2 is a modification including a reference chamber.

In the embodiment illustrated in FIG. 2, there is provided parallel to the path of flow of the object of measurement, a reference chamber 60 communicating with the measuring chamber 30. This arrangement enables the generator of a measuring signal M which is independent of the absolute fluctuations of radiation intensity. The measuring signal M is computed in a conventional manner, for example by means of quotient formation in a computer C of a reference signal R derived from the reference chamber 60, and the measuring signal A' derived in the measuring chamber 30. The reference chamber 60 can operate either under standard conditions independently of the object of measurement or as in the illustrated example, the measured substance flows also through the reference chamber. In the latter case, the indicator space in the reference chamber must be designed such as to remain unaffected by the measured substance.

In another modification, shown in FIGS. 4 and 4a, the indicator space 33 has locally differentiated K values (quenching values) as shown on the abscissa in the plot diagram of FIG. 4a. In the diagram, the vertical axis 33" corresponds to the length of the indicator space 33 and a scale of K values starting from an initial value $K_o$, is on the horizontal axis K'. The K values at different locations of the indicator space are indicated by plotted line K". In this case the indicator space is shiftable relative to the light beam 37 in the direction of arrow 38 and represents the beforementioned variator of the quenching constant K. The position adjustment of the indicator space is made in response to the noise component of the output signal A" applied to a indicator. The correct K value is adjusted when the noise signal component is minimized.

For clarification of the K value adjustment it will be noted that the fluorescent quenching, according to Stern-Vollmer proceeds according to the following equation:

$$I(p) = I_o/1 + Kp \qquad (1)$$

wherein $I_o$ is fluorescence intensity in the absence of the object of measurement, I(p) is fluorescence in the presence of the object of measurement, K is quenching constant and p is concentration value of the object of measurement.

From the above equation, the measuring sensitivity S(P) results as:

$$S(P) = dI/dp = k \cdot I_o(1+Kp)^2. \qquad (b\ 2)$$

The functions S(P) representing the measuring sensitivity for various values of the quenching constant K intersect in the range of larger measuring values. In this manner, by adjusting the K values (for example by locally differentiated material composition of the indicator space), the noise component of the output signal can be minimized for a particular measuring value.

From the above equation (1) a linear form of the measuring sensitivity or fluorescent indicators of low sensivity results as follows:

$$I(p) = (1 - K \cdot p)I_o. \qquad (3)$$

It will be understood that each of the elements described above, or two or more together, may also find a useful application in other types of constructions differing from the types described above.

While the invention has been illustrated and described as embodied in specific examples of fluorometric arrangement, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A fluorometer comprising a transmitter of a monochromatic light beam, the transmitter including a semiconductive light emitting diode, a receiver of a monochromatic light beam, the receiver including a semiconductive photoelectric device, a measuring chamber enclosing an indicator space including fluorescent indicating means, and means for introducing an object of measurement in effective contact with the indicator space, the transmitter having a light output side and the receiver having a light input side, said light output and input sides being arranged opposite each other and the measuring chamber being arranged therebetween so that the distance between the transmitter and the receiver corresponds substantially to the thickness of the measuring chamber, and means for adjusting spacing between said transmitter, said measuring chamber and said receiver.

2. A fluorometer as defined in claim 1, wherein both the light emitting diode and the semiconductive photoelectric device include a monochromatic filter.

3. A fluorometer as defined in claim 1, wherein the fluorescent indicating means includes fluorescent indicators whose quenching coefficient is locally differentiated, and the indicator space being shiftable transversely with respect to the light beam from the transmitter.

4. A fluorometer as defined in claim 1, wherein the fluorescent indicating means includes fluorescent indicators whose quenching constant is less than $10^{-3}$ Torr.

5. A fluorometer as defined in claim 1, wherein the measuring chamber communicates with said introducing means is in the form of a throughflow chamber.

6. A fluorometer as defined in claim 5 wherein said introducing means includes a flowmeter.

7. A fluorometer as defined in claim 1, wherein the measuring chamber includes opposite windows facing respectively the transmitter and the receiver, the windows being in the form of monochromatic filters.

8. A fluorometer as defined in claim 1, wherein the measuring chamber communicates with a reference chamber including fluorescent indicating means defining a reference indicator space, a reference monochromatic light receiver arranged opposite the reference indicator space, the monochromatic light transmitter being positioned and arranged to transmit a test light beam both to the measuring chamber and to the reference chamber, and means for computing a quotient from output signals of the measuring light receiver and the reference light receiver to provide an indication which is independent of fluctuations of the light intensity.

9. A fluorometer as defined in claim 8, wherein the fluorescent indicating means includes fluorescent indicators at a concentration which absorbs the monochromatic test light beam before it reaches the light receiver.

10. A fluorometer as defined in claim 8, further comprising means for focussing the test light beam from the transmitter.

11. A fluorometer as defined in claim 1 further comprising means for adjusting the thickness of said measuring chamber.

12. A fluorometer as defined in claim 1 wherein said indicator space is arranged at a side of said measuring chamber facing said receiver.

* * * * *